(12) United States Patent
Cherepy et al.

(10) Patent No.: US 8,698,086 B2
(45) Date of Patent: Apr. 15, 2014

(54) HIGH EFFECTIVE ATOMIC NUMBER POLYMER SCINTILLATORS FOR GAMMA RAY SPECTROSCOPY

(75) Inventors: Nerine Jane Cherepy, Oakland, CA (US); Robert Dean Sanner, Livermore, CA (US); Stephen Anthony Payne, Castro Valley, CA (US); Benjamin Lee Rupert, Berkeley, CA (US); Benjamin Walter Sturm, Pleasanton, CA (US)

(73) Assignee: Lawrence Livermore National Security, LLC, Livermore, CA (US)

( * ) Notice: Subject to any disclaimer, the term of this patent is extended or adjusted under 35 U.S.C. 154(b) by 60 days.

(21) Appl. No.: 13/162,503

(22) Filed: Jun. 16, 2011

(65) Prior Publication Data

US 2011/0315885 A1 Dec. 29, 2011

Related U.S. Application Data

(60) Provisional application No. 61/357,710, filed on Jun. 23, 2010.

(51) Int. Cl.
| | |
|---|---|
| *G01T 1/20* | (2006.01) |
| *H01L 27/146* | (2006.01) |
| *C09K 11/06* | (2006.01) |
| *C07K 14/005* | (2006.01) |

(52) U.S. Cl.
CPC ................... *C07K 14/005* (2013.01)
USPC ... 250/362; 250/370.09; 250/367; 250/361 R; 252/301.17; 252/301.18; 252/301.35

(58) Field of Classification Search
USPC .................... 250/361 R–362, 367; 252/301.17–301.18, 301.35
See application file for complete search history.

(56) References Cited

U.S. PATENT DOCUMENTS

| | | | | |
|---|---|---|---|---|
| 3,041,287 | A | * | 6/1962 | Hyman, Jr. ................ 252/301.18 |
| 3,609,093 | A | * | 9/1971 | Harrah ........................... 252/586 |
| 5,420,959 | A | * | 5/1995 | Walker et al. .................. 385/143 |
| 5,606,638 | A |   | 2/1997 | Tymianski et al. |
| 6,855,270 | B2 |   | 2/2005 | Mumper et al. |
| 7,067,079 | B2 |   | 6/2006 | Bross et al. |
| 7,547,887 | B2 |   | 6/2009 | Ramsden et al. |
| 7,608,829 | B2 | * | 10/2009 | Loureiro et al. .......... 250/361 R |
| 2004/0004196 | A1 | * | 1/2004 | DeMeo et al. .............. 250/516.1 |
| 2004/0252955 | A1 | * | 12/2004 | Kajiwara et al. .............. 385/120 |
| 2006/0081782 | A1 | * | 4/2006 | Guillebaud et al. ........ 250/360.1 |
| 2007/0069636 | A1 | * | 3/2007 | Choulis et al. ................ 313/504 |
| 2009/0302195 | A1 |   | 12/2009 | Muenchausen et al. |
| 2011/0192981 | A1 | * | 8/2011 | Menge et al. .................. 250/362 |
| 2011/0303852 | A1 | * | 12/2011 | Menge ........................... 250/367 |

OTHER PUBLICATIONS

Chemical Abstract Service (CAS), Molecule of the Week—Mar. 26, 2007—"Triphenyl Bismuth", available online at http://www.cas.org/motw/triphenylbismuth.html.*

(Continued)

*Primary Examiner* — David Porta
*Assistant Examiner* — Jeremy S Valentiner
(74) *Attorney, Agent, or Firm* — Dominic M. Kotab

(57) ABSTRACT

A scintillator material according to one embodiment includes a bismuth-loaded aromatic polymer having an energy resolution at 662 keV of less than about 10%. A scintillator material according to another embodiment includes a bismuth-loaded aromatic polymer having a fluor incorporated therewith and an energy resolution at 662 keV of less than about 10%. Additional systems and methods are also presented.

33 Claims, 12 Drawing Sheets

(56) References Cited

OTHER PUBLICATIONS

The International Search Report from Korea, mailed May 31, 2012 for PCT/US2011/040846, filed Jun. 17, 2011 (3 pages).
The Written Opinion of the International Searching Authority from Korea, mailed May 31, 2012 for PCT/US2011/040846, filed Jun. 17, 2011 (5 pages).
U.S. Appl. No. 12/940,486, filed Nov. 10, 2010.
Britvich et al., "New Heavy Plastic Scintillators," Copyright 2000 by Britvich, Vasil'chenko, Lapshin, Solov 'ev, Instruments and Experimental Techniques, vol. 43, No. 1, 2000, pp. 36-39.
Chatterjee et al., "X-ray contrast polymers of p-styryldi (p-tolyl) bismuth: synthesis and properties," Copyright 1995 Elsevier Sciences, Ltd., Polymer, vol. 36, No. 11, 1995, pp. 2289-2296.
Baroni et al., "Addition of Hetero-Organic Compounds to Polystyrene," Translated from Atomnaya Energiya, vol. 17, No. 6, pp. 1261-1264, Dec. 1964.

Campbell et al., "Efficient plastic scintillators utilizing phosphorescent dopants," Copyright 2007 American Institute of Physics, Applied Physics Letters, vol. 90, 2007, pp. 012117/1-012117/3.

Thompson, Mark, "The Evolution of Organometallic Complexes in Organic Light-Emitting Devices," MRS Bulletin, vol. 32, Sep. 2007, www.mrs.org/bulletin, pp. 694-701.
International Preliminary Report on Patentability from PCT Application No. PCT/US2011/040846 dated Jan. 10, 2013.

\* cited by examiner

| Sample number | high Z | dye | rel LY |
|---|---|---|---|
| V-103-3 | 25% Bi | DPA | 0.34 |
| V-103-4 | 25% Bi | POPOP | 0.32 |
| V-105-1 | 15% Bi | TPB | 0.46 |
| V-105-2 | 35% Bi | TPB | 0.40 |
| Ben#4 / 146-1 | 25% Bi | Ir-complex | 0.57 |
| EJ208 | | | 1 |

| Sample | Matrix | Fluor | BiPh₃ Wt. % | βLY (Ph/MeV) | Relative Gamma Light Yield, 662 keV | Resolution FWHM, 662 keV | Resolution, FWHM, 59.5 keV |
|---|---|---|---|---|---|---|---|
| 1a | PVK | 3% DPA | 40% | 11880 | 0.66 | 9% | 39% |
| 2a | PVK | 3% FIrpic | 40% | 30641 | 0.78 | 6.8 % | 26% |
| 2c | PVK | 3% FIrpic | - | 24191 | 0.73 | 9%* | 30% |
| Eljen EJ208 | PVT | Proprietary | - | 17000 | 1.0 | 8%* | 30% |

*from fit to Compton edge

FIG. 10

| % Iridium Dye (By Weight) | % BiPh$_3$ (By Weight) | Light Yield (Photons per MeV) |
|---|---|---|
| 0% | 0% | 1,420 |
| 0% | 25% | 0 |
| 0% | 40% | 0 |
| 1% | 0% | 17,400 |
| 1% | 25% | 22,069 |
| 1% | 40% | 25,464 |
| 3% | 0% | 24,191 |
| 3% | 25% | 25,464 |
| 3% | 40% | 30,641 |

FIG. 15

HIGH EFFECTIVE ATOMIC NUMBER POLYMER SCINTILLATORS FOR GAMMA RAY SPECTROSCOPY

RELATED APPLICATIONS

This application claims priority to provisional U.S. patent application Ser. No. 61/357,710 filed on Jun. 23, 2010, which is herein incorporated by reference.

The United States Government has rights in this invention pursuant to Contract No. DE-AC52-07NA27344 between the United States Department of Energy and Lawrence Livermore National Security, LLC for the operation of Lawrence Livermore National Laboratory.

FIELD OF THE INVENTION

The present invention relates to gamma ray spectroscopy, and more particularly to gamma ray spectroscopy materials, systems and methods.

BACKGROUND

Detection and classification of gamma ray emitters has attained heightened importance in the protection of vulnerable targets and populaces from special nuclear materials. Many fissionable special nuclear materials emit gamma rays, due to radioactive decay of the elements therein. However, many less harmful and non-fissionable materials also emit gamma rays. Therefore, it is desirable to be able to identify, and whenever possible, distinguish between the types of gamma ray emitters in an unknown material, possibly further concealed inside of a container or vehicle of some type, such as a car, van, cargo container, etc.

Many types of materials emit gamma rays that appear very close together in a gamma spectrum. Scintillator detectors use materials that emit bursts of light when gamma rays interact with the atoms in the scintillator material. The amount of light emitted in a given scintillation pulse can be used to identify the isotope that is emitting the gamma rays. Scintillator detectors may also be used to detect other types of radiation, such as alpha, beta, neutron and x-rays.

Detection sensitivity for weak gamma ray sources and rapid unambiguous isotope identification is principally dependent on energy resolution, and is also enhanced by high effective atomic number of the detector material. High energy resolution scintillator detectors are useful for resolving closely spaced gamma ray lines in order to distinguish between different gamma-emitting radioisotopes. Generally, gamma ray detectors are characterized by their energy resolution. Resolution can be stated in absolute or relative terms. For consistency, all resolution terms are stated in relative terms herein. A common way of expressing detector resolution is with Full Width at Half Maximum (FWHM). This equates to the width of the gamma ray peak on a spectral graph at half of the highest point on the peak distribution.

Plastic scintillator detectors are widely used for scintillation counting, but due to their low efficiency of photoelectric absorption, are rarely used for gamma ray spectroscopy. Unfortunately plastic scintillators also have low light yields, and more importantly, their low effective atomic number, or "$Z_{\it{eff}}$" results in poor photopeak efficiency, and they therefore have not been used for gamma-ray spectroscopy.

Without wishing to be bound by any theory, it is believed that the foregoing deficiency is due to the following. When excitons are created from high energy radiation, the high energy radiation travels through the plastic, creating a cascade of excitations, which in turn produces excitons in which there is a distribution of triplet and singlet excitons. The ratio at which these excitons are produced is material-dependent, and it is believed that the ratio is about 3 to 1, meaning there are three times more triplets than singlets being formed, which severely diminishes the luminescence light yield of the material due to the fact that standard plastic scintillators contain an emitting dye, or fluor, which is a singlet emitter. The fluor collects singlet excitons and re-emits them, generally disregarding the triplets, thus losing the majority of the excitation. Therefore, the addition of a high Z component, has in the past, reduced the scintillation light yield of the plastic due to the fact that singlet excitons in the material are converted into triplets, via spin-orbit coupling to the high Z component, and since these triplet excitons cannot be collected by the singlet emitter, thus reducing the light yield in proportion to the concentration of high-Z constituent.

Attempts to increase this effective Z by doping with heavy metals to induce a photopeak have been made in the past. It was believed that if it were possible to add a sufficient amount of high Z to a plastic, that one would consequently be able to achieve gamma ray spectroscopy which is normally only possible if there is a high photoelectric cross section of the material that produces a very specific peak, the photo peak that appears in materials with that property. The photo electric cross section scales as $Z_{\it{eff}}^4$. Unfortunately, these high Z additives also have a greatly undesirable property in organic photochemistry.

Particularly, studies of loading plastic scintillators with high atomic number organometallics in the past have encountered light yield reductions and yellowing or browning of the scintillator material upon addition of sufficient organometallic to provide photoelectric absorption enhancement.

Accordingly, it is presently widely believed that it is impossible to create a plastic scintillator that provides sufficient resolution for gamma ray spectroscopy.

SUMMARY

A scintillator material according to one embodiment includes a bismuth-loaded aromatic polymer having an energy resolution at 662 keV of less than about 10%.

A scintillator material according to another embodiment includes a bismuth-loaded aromatic polymer having a fluor incorporated therewith and an energy resolution at 662 keV of less than about 10%.

A scintillator radiation detector system according to one embodiment may include a scintillator material as recited above; and a processing device for processing pulse traces corresponding to light pulses from the scintillator material.

A scintillator radiation detector system according to one embodiment may include a scintillator material as recited above; and a processing device for generating radiological image data based on pulse traces corresponding to light pulses from the scintillator material.

A method according to one embodiment includes processing pulse traces corresponding to light pulses from a scintillator material, the scintillator material comprising: a bismuth-loaded aromatic polymer having an energy resolution at 662 keV of less than about 10%; and outputting a result of the processing.

A method according to another embodiment includes mixing a bismuth organometallic complex with an aromatic monomer or polymer and at least one fluor; and processing the mixture for creating a bismuth-loaded aromatic polymer.

Other aspects and embodiments of the present invention will become apparent from the following detailed descrip-

BRIEF DESCRIPTION OF THE DRAWINGS

FIG. 10 is a table showing measured values for materials used in one embodiment.

FIG. 15 is a table showing measured light yields for different tested embodiments of a plastic scintillator.

DETAILED DESCRIPTION

The following description is made for the purpose of illustrating the general principles of the present invention and is not meant to limit the inventive concepts claimed herein. Further, particular features described herein can be used in combination with other described features in each of the various possible combinations and permutations.

Unless otherwise specifically defined herein, all terms are to be given their broadest possible interpretation including meanings implied from the specification as well as meanings understood by those skilled in the art and/or as defined in dictionaries, treatises, etc.

It must also be noted that, as used in the specification and the appended claims, the singular forms "a," "an" and "the" include plural referents unless otherwise specified.

The following description describes several embodiments relating to polymer scintillator materials with sufficiently high effective atomic number and sufficiently high light yield that they exhibit good photopeak efficiency and they may be used to directly obtain gamma ray spectra. Methods of fabrication thereof are also presented.

In one general embodiment, a scintillator material includes a bismuth-loaded aromatic polymer having an energy resolution at 662 keV of less than about 10%.

In another general embodiment, a scintillator material includes a bismuth-loaded aromatic polymer having a fluor incorporated therewith and an energy resolution at 662 keV of less than about 10%.

In one general embodiment, a scintillator radiation detector system includes a scintillator material as recited herein; and a processing device for processing pulse traces corresponding to light pulses from the scintillator material.

In another general embodiment, a scintillator radiation detector system includes a scintillator material as recited herein; and a processing device for generating radiological image data based on pulse traces corresponding to light pulses from the scintillator material.

In one general embodiment, a method includes processing pulse traces corresponding to light pulses from a scintillator material, the scintillator material comprising: a bismuth-loaded aromatic polymer having an energy resolution at 662 keV of less than about 10%; and outputting a result of the processing.

In another general embodiment, a method includes mixing a bismuth organometallic complex with an aromatic monomer or polymer and at least one fluor; and processing the mixture for creating a bismuth-loaded aromatic polymer.

General Scintillator-Based Radiation Detector System

Figure 1:
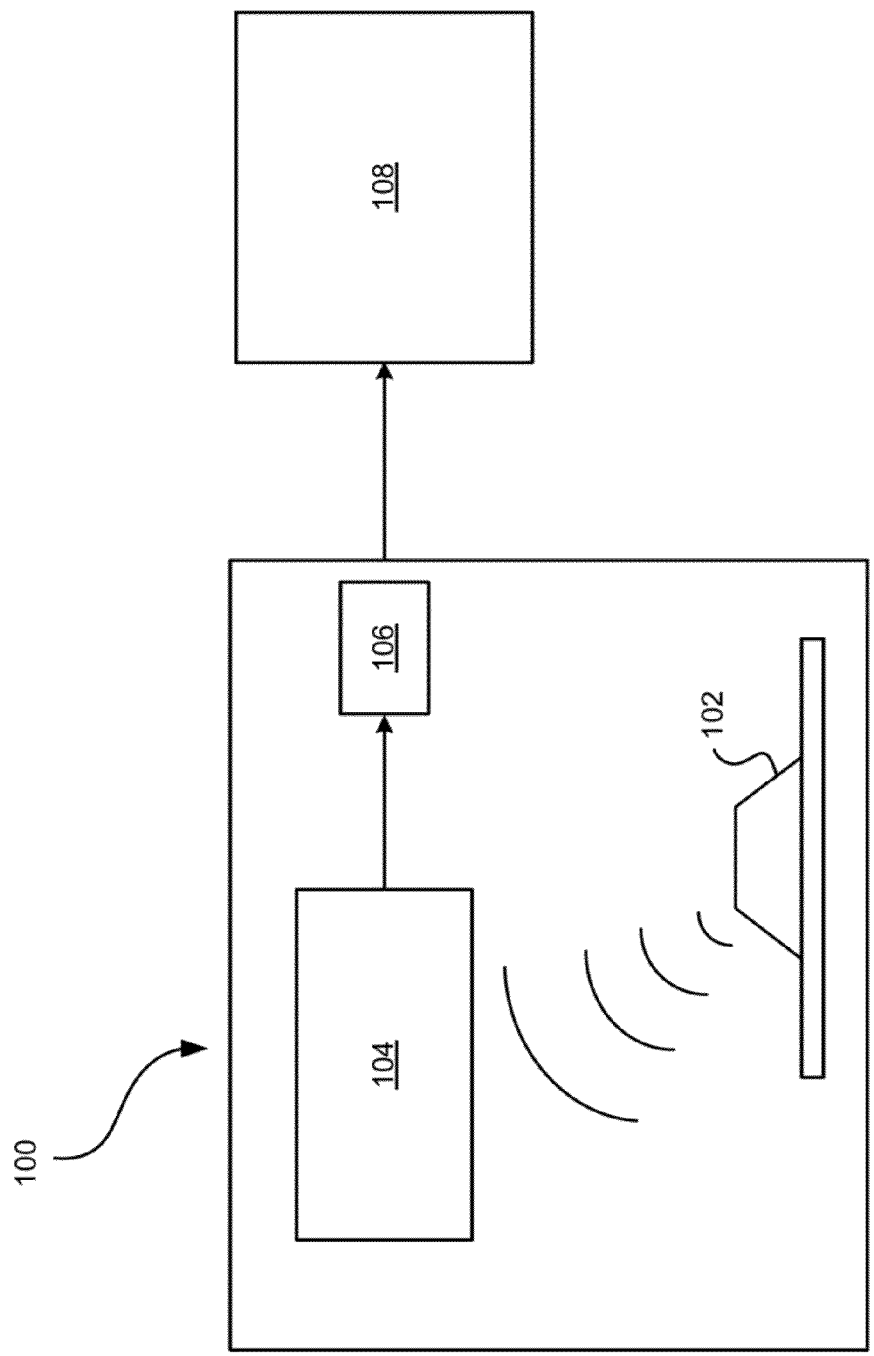
FIG. 1 is a simplified schematic layout of a spectroscopy system according to one embodiment.

FIG. 1 depicts a simplified spectroscopy system according to one embodiment. The system 100 comprises a scintillator material 102, such as of a type described herein, and which is referred to herein interchangeably as a scintillator. The system 100 also includes a photodetector 104, such as a photomultiplier tube or other device known in the art, which can detect light emitted from the scintillator 102, and detect the response of the material to at least one of neutron and gamma ray irradiation.

The scintillator 102 produces light pulses upon occurrence of an event, such as a gamma ray or other radiation engaging the scintillator 102. As the gamma ray, for example, traverses the scintillator 102 and is absorbed, photons are released, appearing as light pulses emitted from the scintillator 102. The light pulses are detected by the photodetector 104 and transduced into electrical signals that correspond to the pulses. The type of radiation can then be determined by analyzing the integral of the light pulses and thereby identifying the gamma ray energy absorbed by the scintillator.

In some embodiments, the system 100 may be, further comprise, or be coupleable/coupled to, a processing device 106 for processing pulse traces output by the photodetector 104. In other embodiments, the system 100 may include a processing device that receives data from a photodetector that is not permanently coupled to the processing device. Illustrative processing devices include microprocessors, field programmable gate arrays (FPGAs), application specific integrated circuits (ASICs), computers, etc.

The result of the processing may be read out and/or stored. For example, the result may be displayed on a display device 108 in any form, such as in a histogram or derivative thereof.

Scintillator Materials

Scintillator materials according to some embodiments are fabricated by polymerization of a matrix material which has dispersed therein a high-Z component and a light-emitting dye (fluor), and in some embodiments other additives.

A scintillator material according to one embodiment includes a bismuth-loaded aromatic polymer having an energy resolution at 662 keV of less than about 10%, where "about X" as used herein, where X is the value, means X±10% of X. In experiments conducted by the inventors, energy resolutions of 6.8% at 662 keV have been achieved, and energy resolutions at least down to about 4% are expected. Thus, in one approach, the energy resolution of the material at 662 keV of between about 10% and 4%.

Polymer Matrix Materials

As noted above, scintillator materials may include a matrix of polymeric material. A scintillator material according to one embodiment includes a polymer having at least one of poly-styrene, poly-vinyltoluene, poly-3-vinyltriphenylamine, poly-4-vinyltriphenylamine and poly-9-vinylcarbazole. Preferably, the polymer of one such embodiment includes poly-9-vinylcarbazole.

It has been found that in one embodiment, polyvinylcarbazole polymer scintillators with high loading of a bismuth organometallic exhibit improved light yields, and are capable of gamma ray spectroscopy. In one approach of the present embodiment, when activated by a standard fluor, diphenylanthracene, a bismuth-loaded polymer produces ~6,000 photons/MeV, exhibits an emission maximum at 420 nm, a ~15 ns decay, and energy resolution of 9% at 662 keV is measured. In another embodiment of a bismuth-loaded polymer when doped with an iridium complex fluor, has been found to have an emission maximum of 500 nm, a decay time of 1.2 s, a light yield of ~30,000 photons/MeV, and energy resolution better than 7% FWHM at 662 keV Without wishing to be bound by any theory, polyvinylcarbazole's superior charge and exciton transport properties are believed to give an increased light yield and proportionality over poly-styrene and poly-vinyltoluene which are used in current commercially available plastic scintillators. It is believed that this may be due to the fact that the band gap of polyvinylcarbazole is slightly smaller than that of polyvinyl toluene and polystyrene so that the triphenyl bismuth does not interfere with the transport of excitons in that material.

A scintillator material according to yet another embodiment includes a polymer of a type known in the art having a polymeric component with a band gap of less than that of poly-vinyltoluene.

In one embodiment for fabricating a scintillator material, the monomer (styrene, vinyltoluene, 9-vinylcarbazole, etc.) is added to a reaction vessel along with a radical initiator. The initiator is typically a peroxide such as tert-butyl peroxide or Luperox 231® (trademark of Arkema), etc. The monomer may comprise about 35-80% by weight, preferably 40-60% by weight of the sample and the initiator from less than 1% by weight to several % by weight. The other additives, discussed below, may also be added and ambient oxygen may be removed by placing the mixture under vacuum followed by refilling with nitrogen gas. The sample is then heated to about 80° C. or higher until solid, typically for several hours. The temperature of 80° C. is significant, especially in the case of the polyvinylcarbazole matrix. Below this temperature the polyvinylcarbazole based samples do not exhibit good transparency, while around 80° C. and above all components of the mixture appear to remain soluble and well mixed through the entire polymerization.

High-Z Component

Figure 2:
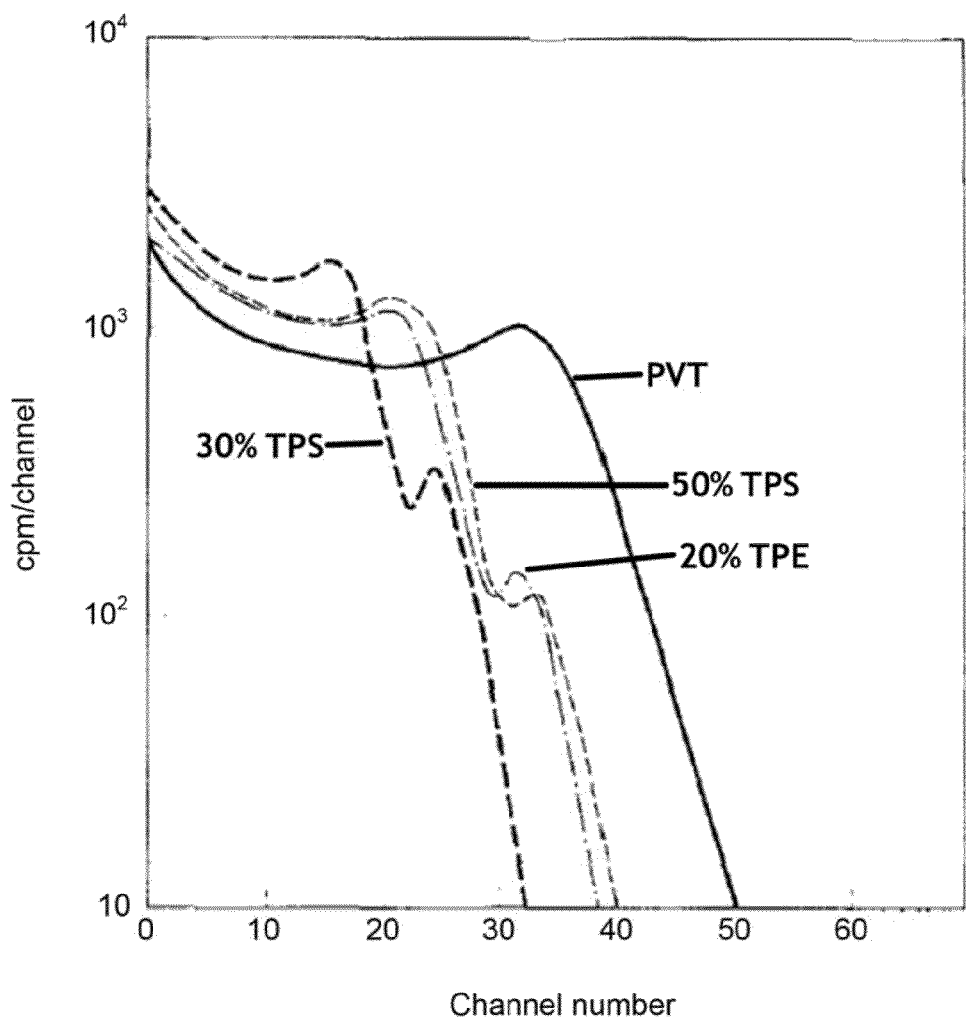
FIG. 2 is a graph showing the gamma spectra of several embodiments of plastic scintillators.

Attempts to add high Z components to different embodiments of plastic scintillators have been made in the past in an effort to improve light yield. However as depicted in FIG. 2, when high Z organics, which include triphenylstyryltin (TPS) and triphenylethyltin (TPE), were added to the polyvinyltoluene (PVT) samples, substantial light quenching and reduction in energy resolution resulted. These results, regularly seen in the past, have brought those skilled in the art to believe that the addition of high Z components to plastic scintillators, directly cause their functionality to greatly decrease.

However, contrary to conventional wisdom and what one skilled in the art would have expected, the inventors have surprisingly found that it is possible to incorporate high-Z components into a polymer-based scintillator material and obtain resolutions that enable gamma ray spectroscopy. Moreover, the inventors have even more surprisingly found that performance of the scintillator may actually increase upon addition of the high-Z material.

Without wishing to be bound to any theory, it is believed that in order to achieve gamma ray spectroscopy, a high loading of a heavy element is required. Furthermore, it is desirable that the high-Z component be mixed homogenously into the polymer matrix for optimum scintillator response and harvesting of light. Bismuth-containing materials, and especially triphenyl bismuth, meet these requirements, and are used in several embodiments. Illustrative embodiments may be loaded with up to 40% or higher by weight of the high-Z component. Exemplary embodiments may include about 5-45% by weight of a high-Z component, 20-40% by weight of a high-Z component, 25-30% by weight of a high-Z component, 35-45% by weight of a high-Z component, etc.

Illustrative bismuth compounds that may be used in various embodiments include, but are not limited to, bismuth alkoxides (e.g. bismuth t-butoxide), bismuth di-aryl chlorides, tri-phenyl bismuth, and tri-aryl bismuth compounds (e.g. tri-tolyl bismuth, tri-dimethylaniline bismuth, tri-dimethoxyphenyl bismuth, etc.).

Particularly preferred embodiments use triphenyl bismuth. Illustrative embodiments may be loaded with up to 25%, 40%, or higher by weight of this material. One of the few drawbacks of this particular material is that it begins to decompose at temperatures above 80° C. resulting in brown and unusable samples. Samples prepared with 25% or higher loading in one of the matrices described above at 80° C., with an appropriate fluor, result in transparent samples with good light yields which are capable of gamma ray spectroscopy. In one embodiment, a bismuth molecule incorporating alternative organic ligands in an attempt to raise the processing temperature of the samples allows for greater control of the system as well as higher loadings of bismuth and fluors and shorter production times of the samples.

Use of organic ligand bismuth complexes which blend homogenously into organic polymers in high loading is a significant advancement in polymer scintillators. In one approach, a bismuth complex which is characterized by a higher solubility and greater thermal stability is used to prevent this complex from decomposing when exposed to high temperatures in instances such as polymerization.

In one embodiment, a bismuth complex without low-lying energy levels allows a polymer to be loaded with an organobismuth compound, therefore providing a supply of high Z, and would not interact electronically. The bismuth complex is very advantageous due to the fact that it is the highest Z element which does not have toxic or radioactive characteristics. In one embodiment, the composition of a polymer with an iridium complex may be combined with a high Z component to further improve the luminescence light yield.

In yet another embodiment, a scintillator material which incorporates both gamma spectroscopy and a fast decay time to improve performance in active interrogation applications. In one approach, a cargo container undergoes active interrogation in which it is irradiated by, in one embodiment, a neutron, or in yet another embodiment, a high energy gamma interrogation source, after which, gammas coming off of the cargo container have their spectral characteristics examined to gather an indication of what elements contained within the container are producing the gamma rays. To make this possible, both a very fast event rates, as well as gamma ray spectroscopy are required, so that the scintillator can have a lower dose rate applied to the object of interest as well as the ability to determine the elemental source of the gamma rays being detected. In yet another approach, a cargo container undergoes passive interrogation which utilizes the present embodiment's gamma spectroscopy to improve detection quality.

In some embodiments, the bismuth may be present in an organometallic complex that is incorporated into the polymer e.g., as by copolymerization, crosslinking, or, alternatively, simply surrounded by the polymer matrix but not chemically linked or coupled thereto.

In one approach for fabricating a scintillator material, a bismuth material, e.g., triphenyl bismuth, tritolyl bismuth, tristyryl bismuth or a mixed ligand material such as ditolylstyryl bismuth, etc. in its solid state, is mixed in with an initiator e.g., peroxide, etc., which is also mixed with the monomer, e.g., vinylcarbazole monomer, in its solid state, as well as the fluor e.g., iridium complex, diphenyl anthracene, etc. in its solid state. The temperature of the mixture is then increased until it reaches the melting point of the monomer, e.g., vinylcarbazole where the initiator causes the vinyl group on the carbazole to react with other vinyl groups forming a polymer matrix in which the fluor, and the triphenyl bismuth are uniformly dispersed throughout. In another approach, the bismuth organometallic complex is structurally characterized as being copolymerized with the polymer.

Furthermore, in yet another such approach, it is possible that the bismuth organometallic complex is not chemically coupled, e.g., by direct co-polymerization with, crosslinked to, etc. to any other component of the polymer.

Fluor

A scintillator material according to one embodiment includes an effective amount of a fluor having a light yield of >10,000 photons/MeV. An effective amount of fluor is at least the quantity of fluor that enables emission of a detectable light event from the scintillator material. In one approach, the fluor may be present in the scintillator material from about 0.1% to about 3% by weight.

One such embodiment may include an organic singlet fluor. Organic floors are desirable in that they have the advantage that they are relatively cheap, emit in the blue part of the visible spectrum where photomultiplier tubes are most sensitive, and have fast response times. The major drawback to these materials is that any triplet excited states that form in the material, which may constitute up to about ¾ of the excited states, may be lost to non-radiative decay.

In one embodiment, the organic fluor has a decay time of less than 10 microseconds and greater than 100 picoseconds.

In yet another approach, the fluor is an organometallic, based on iridium, platinum, osmium, bismuth or other high-Z luminescent organometallic complex. In order to significantly increase light yields, in separate samples, iridium containing fluors, such as those used in the OLED (organic light emitting diode) industry, are incorporated. These materials are capable of emitting light from both the singlet and triplet excited states and therefore may exhibit light yields up to about 3× that of the traditional organic fluors. The higher light yield is especially important in gamma-ray spectroscopy. In one illustrative embodiment, polyvinyl carbazole, with a high loading of bismuth, and with both singlet emitting organic dyes and triplet emitting iridium-complex dyes, provides excellent results for gamma radiation detection.

A scintillator material according to yet another embodiment includes an effective amount of at least two different fluors. The two different fluors may be present in any ratio relative to one another. In one approach, one of the fluors is an organometallic fluor. This approach allows for the energy to transfer from one fluor to the other, to ensure that the photons being captured are reabsorbed and reemitted properly.

Detection

A scintillator radiation detector system according to one embodiment includes a scintillator material; and a processing device for processing pulse traces corresponding to light pulses from the scintillator material. Any type of photodetector and signal processing known in the art may be performed. Moreover, any type of processing device may be used. The system may include one or more components shown in FIG. 1.

A scintillator radiation detector system according to another embodiment includes a scintillator material; and a processing device for generating radiological image data, e.g., that may be used to create a radiological image, based on spatially defined pulses corresponding to shadowography of an object under irradiation by an x-ray or gamma ray source detected via light pulses from the scintillator material. A radiation detection image may also be acquired based on mapping of specific radioisotopes, as the medical imaging techniques known as PET and SPECT. Any type of processing known in the art may be performed. Moreover, any type of processing device may be used. The system may include one or more components shown in FIG. 1.

Figure 3:
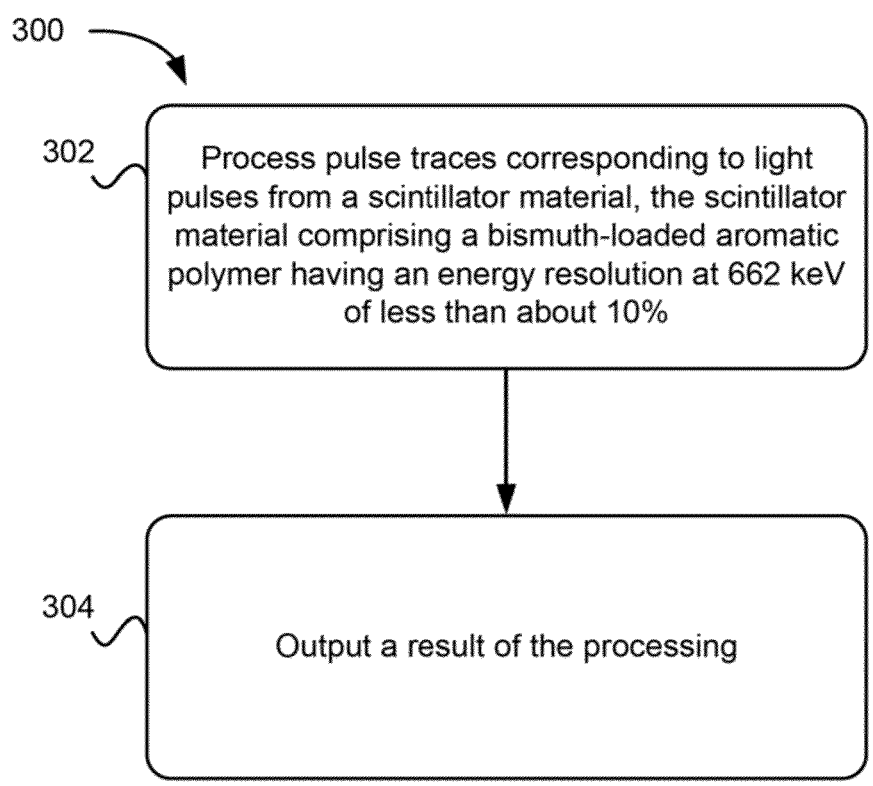
FIG. 3 is a flowchart showing the method of processing an event according to one embodiment.

A method 300 according to one embodiment depicted in FIG. 3 includes processing pulse traces corresponding to light pulses from a scintillator material, which in one approach is comprised of a bismuth-loaded aromatic polymer having an energy resolution at 662 keV of less than about 10% 302; and outputting a result of the processing 304. Any type of processing known in the art may be performed. Any type of output known in the art may be performed. Examples of processing and output which may be used in conjunction with some embodiments are detailed in U.S. patent application Ser. No. 12/940,486, filed Nov. 10, 2010, and which is herein incorporated by reference.

Figure 4:
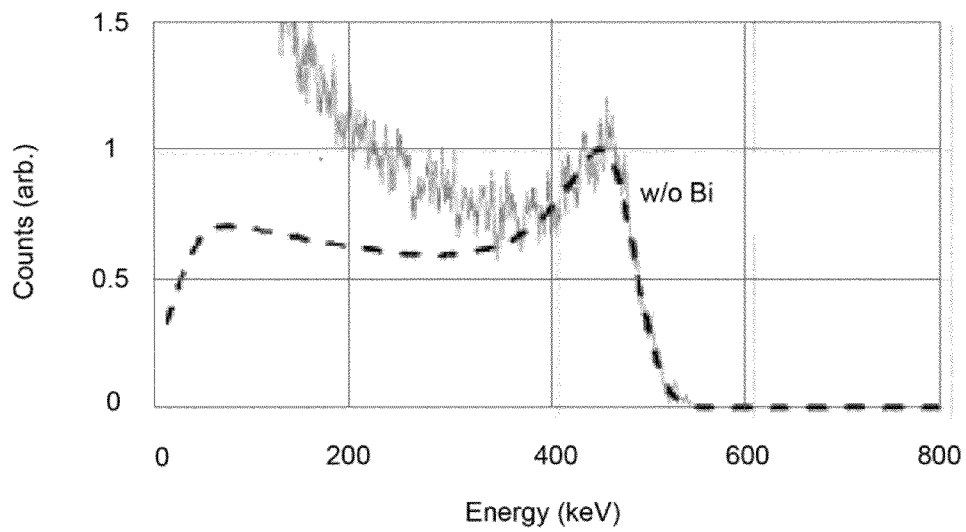
FIG. 4 is a graph showing the gamma ray pulse-height spectra acquired for one embodiment.

FIG. 4 depicts the gamma ray pulse-height spectra acquired in one embodiment, with the monoenergetic Cs-137 source at 662 keV for commercial plastic scintillator, EJ208, and reveals the lack of a photopeak. However, the Compton edge may be fit and analyzed to reveal that this material would be capable of offering about 8% resolution at 662 keV if the photoelectric cross-section could be improved.

Figure 5:
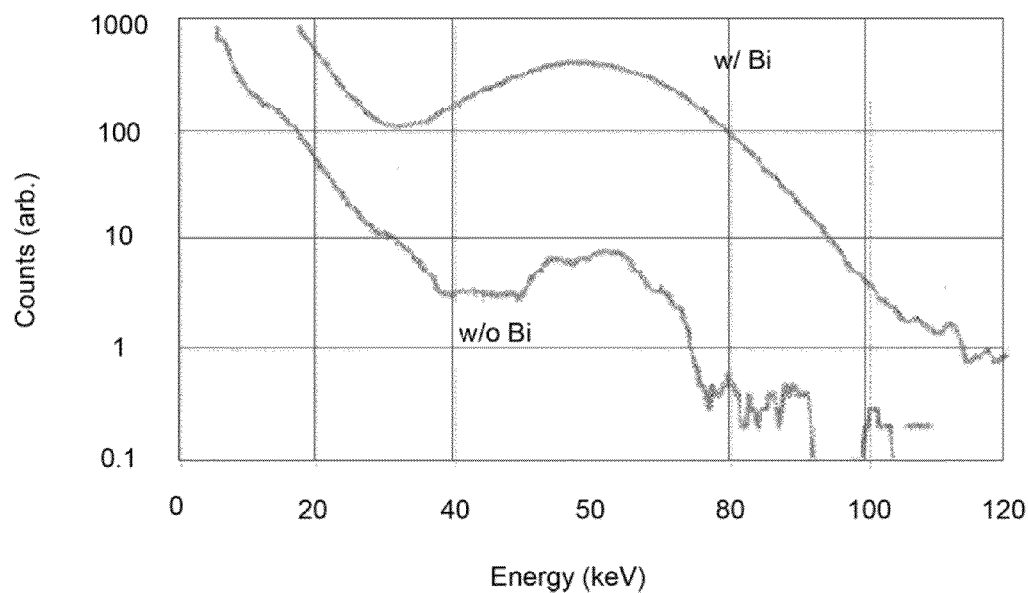
FIG. 5 is a graph showing a pulse height spectrum acquired for one embodiment.

Furthermore, FIG. 5 depicts a pulse height spectrum acquired for another embodiment at 662 keV for a 40 wt % triphenyl bismuth loaded polymer scintillator, fabricated at LLNL, reveals a clear photopeak. Although the escape peak dominates the feature, at 70% of the events, and appears at 585 keV (the two Bi K-α x-rays are at 74.5 and 77 keV), while the 662 keV feature comprises about 30% of the events. This is due to the small size of our current samples, only about 1 $cm^3$.

Figure 6:
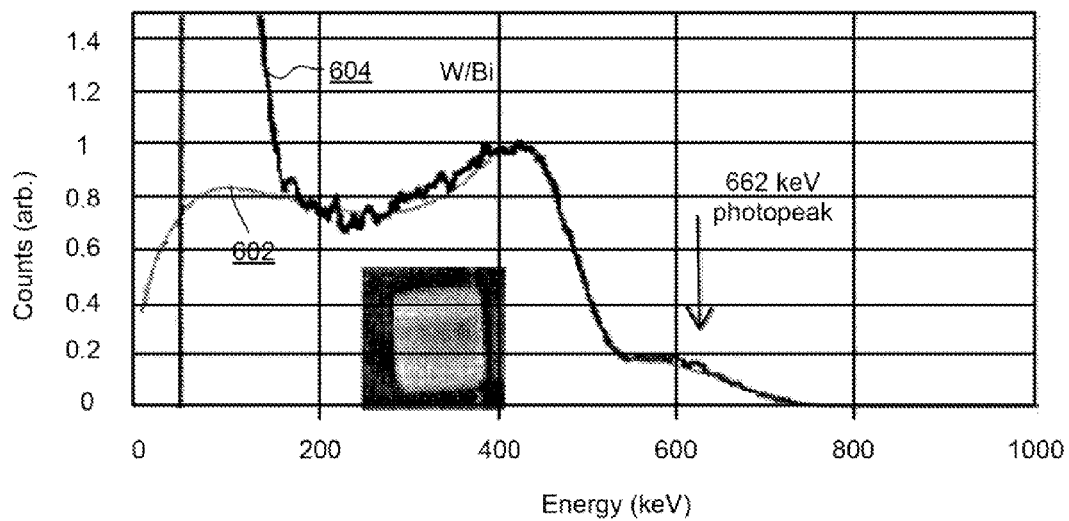
FIG. 6 is a graph showing a photopeak at lower energies for one embodiment.

It is noted that at lower energies, even commercial plastic possesses a photoelectric cross-section sufficient to produce a photopeak, as shown in FIG. 6 with a 60 keV Am-241 source. See line 602. Shown also is the response 604 of an embodiment of a Bi-loaded sample, in which the photopeak is about 50× stronger than for the standard plastic scintillator.

Figures 7, 8:
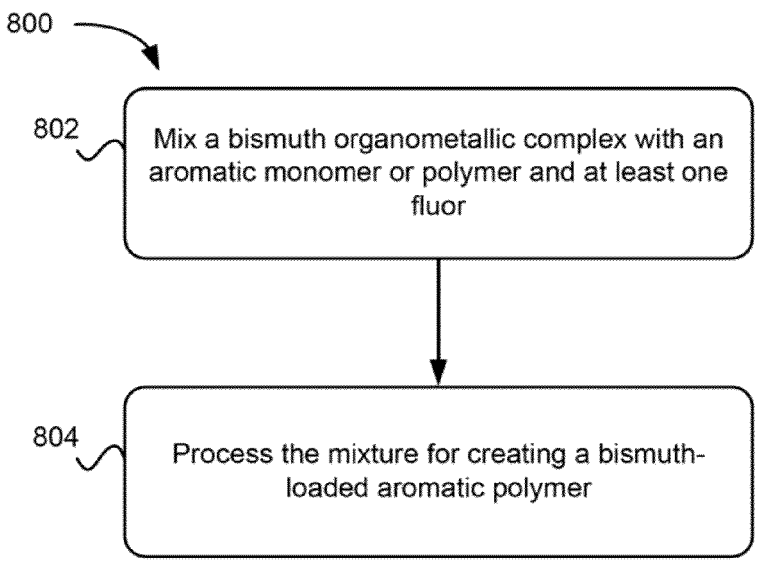
FIG. 7 is a table showing several embodiments of plastic scintillators which exhibit photopeaks.
FIG. 8 is a flowchart showing a method of creating a bismuth-loaded aromatic polymer according to one embodiment.

Additionally, FIG. 7 is a table which depicts several further embodiments of Bi-loaded plastic scintillator fabricated at LLNL that exhibit a clear photopeak when excited at 662 keV, and their light yields, compared to commercial plastic scintillator. Energy resolution of <15% at 662 keV is typical for a sample characterized based on polyvinylcarbazole, and activated with a variety of fluors, as listed in FIG. 7 showing several embodiments of Bi-loaded plastic scintillators which exhibit a clear photopeak in contrast with commercial plastic scintillators. So far, light yields, when a singlet fluor is utilized, have been found to decrease as a function of concentration of organobismuth, nevertheless, at 25 wt % triphenyl bismuth, the material is able to exhibit a clear photopeak, though it offers a light yield that is about half that of commercial polyvinyl toluene scintillators.

A method 800 according to another embodiment depicted in FIG. 8 includes mixing a bismuth organometallic complex with an aromatic monomer or polymer and at least one fluor 802; and processing the mixture for creating a bismuth-loaded aromatic polymer 804.

In one approach, the bismuth organometallic complex is copolymerized with the monomer to form the bismuth-loaded aromatic polymer.

In yet another approach, the processing includes causing the monomer or polymer to crosslink, wherein the bismuth organometallic complex is not chemically coupled to any other component of the bismuth-loaded aromatic polymer.

Experimental

Following is a description of experimental procedures, results and observations. The following description is provided by way of example only, and in no way is meant to be limiting.

Figure 9A:
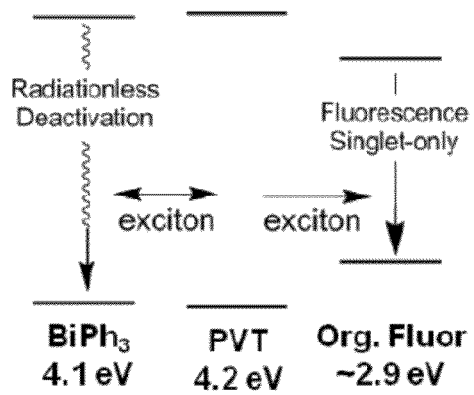
FIG. 9A is a graph showing the energy levels of materials used in one embodiment.
Figure 9B:
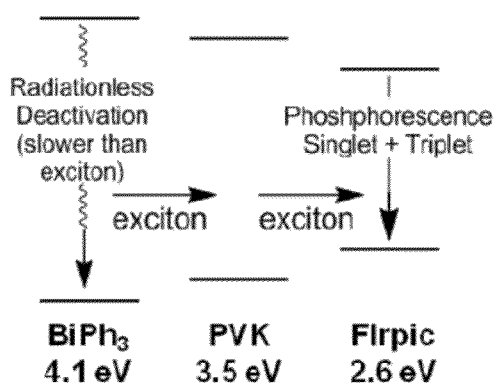
FIG. 9B is a graph showing the energy levels of materials used in one embodiment.
Figure 9C:
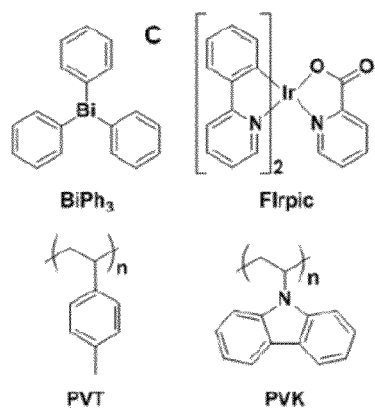
FIG. 9C is a structural representation of materials used in one embodiment.

In one study, the materials that were chosen were, polyvinylcarbazole (PVK) as the polymer matrix (bandgap 3.5 eV), triphenyl bismuth (BiPh$_3$) as the high-Z dopant, and two different fluors, a standard organic fluor, diphenylanthracene (DPA), and an Er-complex, FIrpic (bandgap 2.6 eV) as the spin-orbit coupling fluor. Additional comparisons were made with a commercial PVT scintillator from Eljen. The materials choices were based on the energy levels of the materials which are shown in FIGS. 9A-9B, the high-Z/volume ratio that the Bi complex can attain in this matrix, combined with its low toxicity and low cost, and the high fluorescence efficiency of FIrpic from both singlet and triplet states. Furthermore, two series of polymer scintillators were made. Samples 1a-c are PVK-based parts with 3% by weight DPA and 40%, 25% and 0% by weight of BiPh$_3$ respectively. In samples 2a-c FIrpic was used as fluor, also 3% by weight. Structures of some the materials used are shown in FIG. 9C and a summary of selected sample compositions and important measured values can be found in FIG. 10.

In the present study, all samples except the Eljen standard were synthesized by bulk polymerization of 9-vinyl carbazole initiated by a peroxide. The monomer, peroxide initiator, BiPh$_3$ and fluor were placed in a polymerization vessel under nitrogen atmosphere and heated overnight. The temperature was maintained between the melting point of 9-vinyl carbazole (65° C.) and the decomposition temperature of BiPh$_3$ (100° C.). The maximum loading of BiPh$_3$ in the PVK based samples was 40% by weight, resulting in $Z_{eff}$=26, above which the Bi compound is not soluble. These compositions gave transparent samples which were light yellow when they contained FIrpic and colorless with DPA. Longer heating times gave darker yellow or brown samples, presumably from the decomposition of BiPh$_3$. Samples were right cylinders, 18 mm in diameter and 2 mm in height after being shaped and polished, except the Eljen standard which was 10 mm by 5 mm.

Figure 11A:
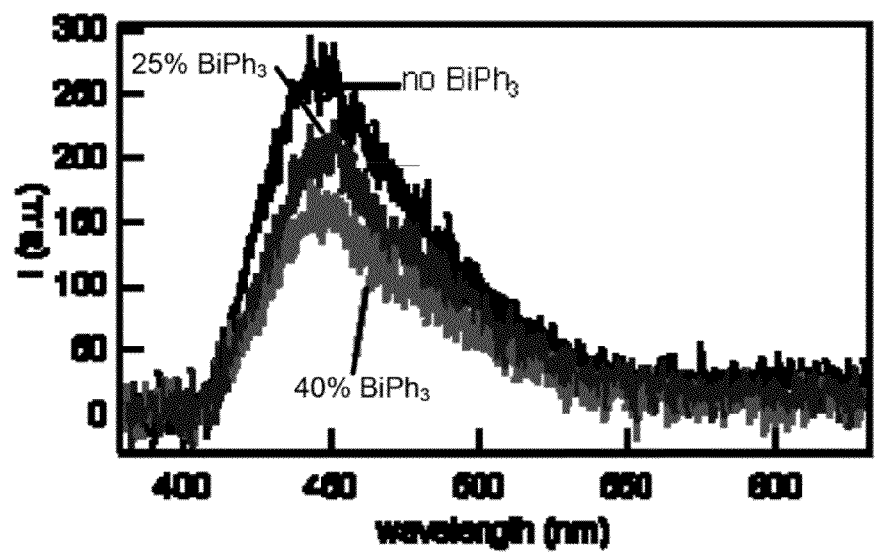
FIG. 11A is a graph depicting the radioluminescence for the PVK/DPA/BiPh$_3$ system decreases as the BiPh$_3$ loading increases.
Figure 11B:
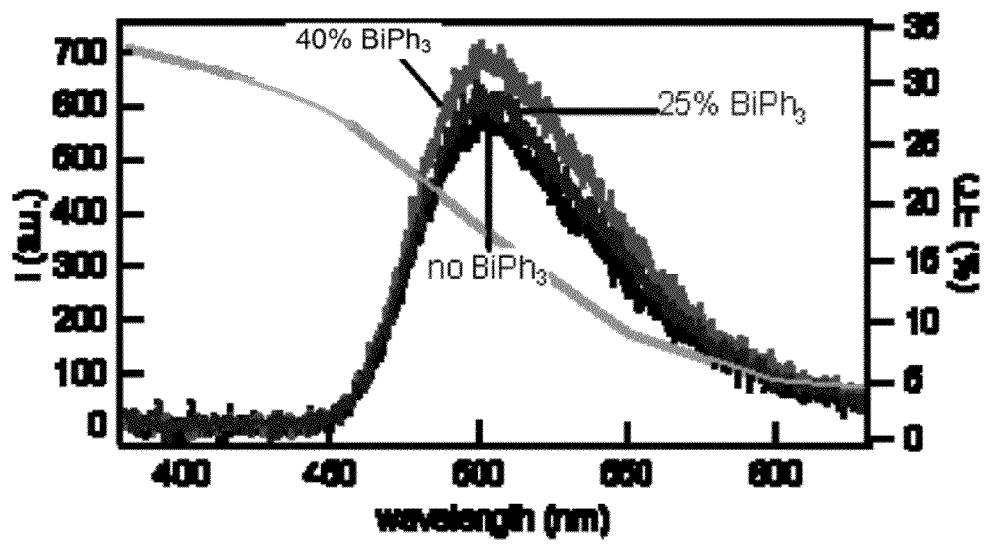
FIG. 11B is a graph depicting the beta radioluminescence spectra acquired with samples of composition PVK/FIrpic/BiPh3 and the spectral response quantum efficiency curve for a super-bialkali photomultiplier tube.

Furthermore, in the present study, the decay lifetimes were acquired using a flashlamp-pumped Nd:YAG laser at 266 nm with 20 ns FWHM pulses. Luminescence was collected with a monochromator coupled to an R928 Hamamatsu photomultiplier tube (PMT) and read out by an oscilloscope. The decay times measured for the DPA and the FIrpic fluors were 14 ns and 1.25 µs, respectively. Radioluminescence spectra were acquired using a $^{90}$Sr/$^{90}$Y source (average beta energy ~1 MeV), and were collected with a Princeton Instruments/Acton Spec 10 spectrograph coupled to a thermoelectrically cooled charge-coupled device (CCD) camera and corrected for spectral sensitivity. All FIrpic-containing samples were found to have higher beta light yields (($\beta$LY) than the Eljen standard, using silicon CCD readout. FIG. 11A shows that the radioluminescence for the PVK/DPA/BiPh$_3$ system decreases as the BiPh$_3$ loading increases. In contrast, FIG. 11B shows the beta radioluminescence spectra acquired with samples 2a-c, of composition PVK/FIrpic/BiPh$_3$ and the spectral response quantum efficiency curve for a super-bialkali photomultiplier tube. All spectra may be compared in an absolute way. When the Ir-complex fluor FIrpic is used, the light yield goes up slightly as a function of Bi-loading. This may be attributable to an increased triplet population with addition of BiPh$_3$, and the efficient emission of both triplet and singlet excitation with the Ir fluor, while with DPA, triplet states decay non-radiatively. In the figure, it can be seen that the standard blue-emitting organic fluors such as DPA are a much better spectral match to the PMT response.

Figure 12A:
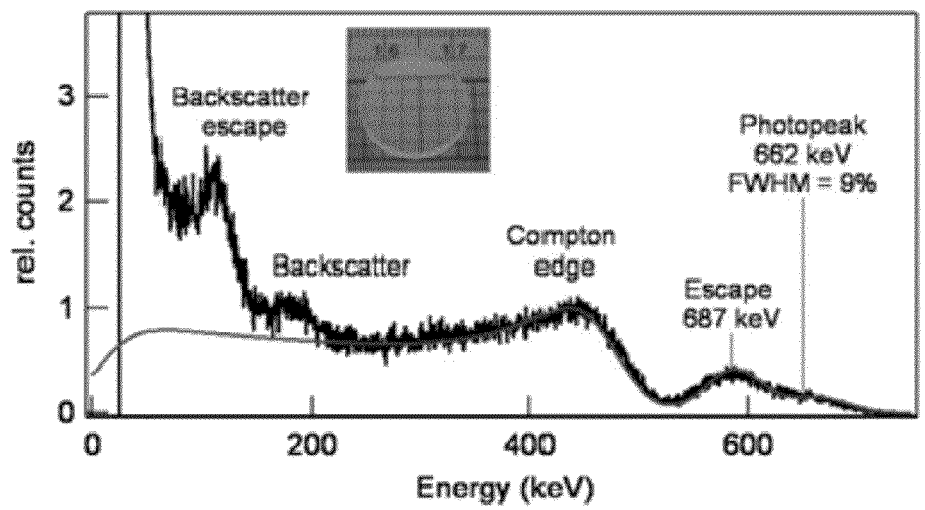
FIG. 12A is a graph showing the pulse height spectra acquired for one embodiment.
Figure 12B:
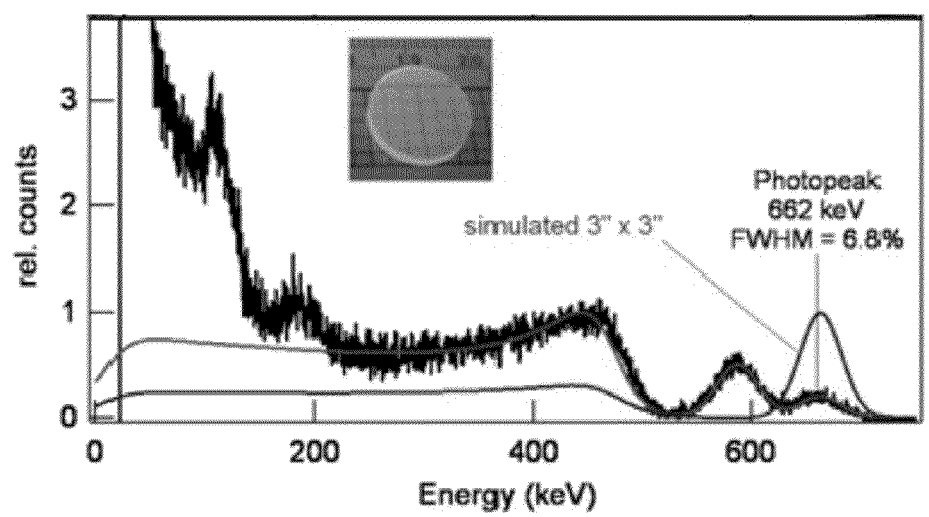
FIG. 12B is a graph showing the FIrpic-activated result for one embodiment.

Additionally, in the present study, gamma ray spectra were acquired using a Hamamatsu R6231-100 superbialkali PMT. Plastic scintillators were centered on the entrance window, optically coupled to the PMT with optical grease and wrapped with several layers of Teflon tape. The PMT signals were shaped with a Tennelec TC 244 spectroscopy amplifier (8 µs shaping time for FIrpic activated samples and 1 µs for DPA activated samples) then recorded with an Amptek MCA8000-A multi-channel analyzer. The spectra were fit with a spectrum simulator to evaluate the Compton edge and photopeak positions (to estimate the scintillation light yield), its energy resolution, assessed by a Gaussian full width at half maximum (FWHM), as well as the escape peak, due to the Bi K-$\alpha$ x-rays. The spectrum simulator utilized is a simple one-dimensional treatment based on the average geometric chord length of the scintillator optic, and incorporates the effects of photoelectric absorption, Compton scattering, Compton scattering followed by photoelectric absorption, double Compton scattering, and double Compton scattering followed by photoelectric absorption. Gamma light yields are determined by direct comparison of the Compton edge with that of an EJ208 sample. FIG. 12A shows the pulse-height spectra acquired using the 662 keV gamma from $^{137}$Cs for the DPA-activated sample 1a, resolution is measured at 9%. This figure additionally exhibits several spectral features, including the photopeak, an escape peak (due to the Bi-209 K x-rays 74.8 and 77.1 keV), the Compton edge, a backscatter peak and the backscatter escape peak. It should also be noted that the inset photo shows the sample used, illuminated by a UV lamp. FIG. 12B shows the Firpic-activated sample 2a, producing resolution of 6.8% at 662 keV. In these samples two peaks are present, a full energy peak and an escape peak corresponding to the loss of a 77 keV x-ray generated when an electron falls in to the vacancy in the core Bi shell created by the photo electron. This escape peak is greater in area than the full energy peak due to the moderate $Z_{eff}$ of the samples and their small volume. The gamma spectra of scintillators of different sizes but the same composition as sample 2a were modeled, and a simulation, shown in FIG. 12B, reveals that a cylindrical sample with diameter and height of 3"×3" should provide only the full energy peak without the presence of an escape peak, as well as offer gamma spectroscopy performance similar to NaI(Tl), the most common scintillator used in practice.

Figure 13:
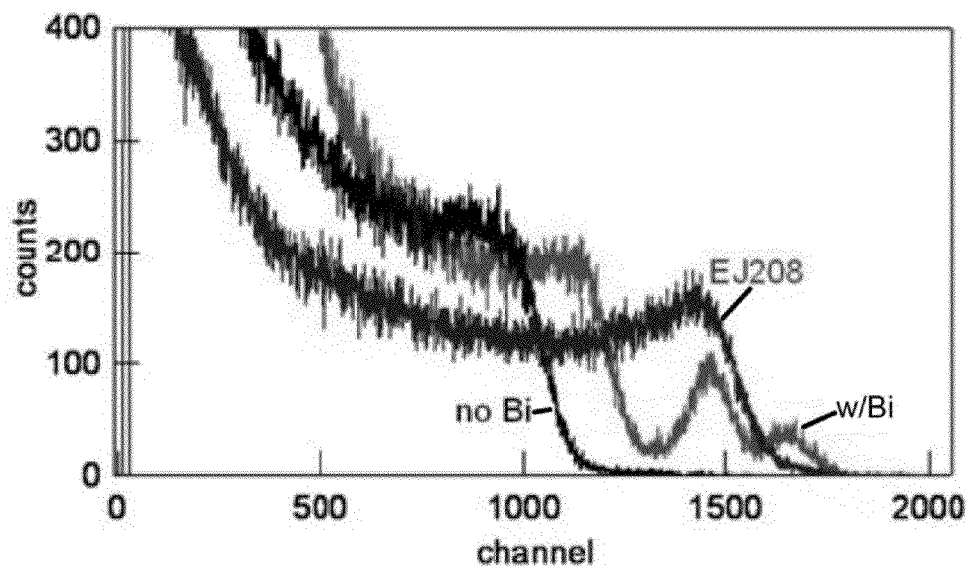
FIG. 13 is a graph showing the pulse height spectra acquired for an embodiment.

In FIG. 13, Cs-137 pulse height spectra of the PVK/FIrpic/BiPh$_3$, 2a, and the PVK/FIrpic, 2c, samples are shown, revealing that although the normalized integrated light yields of these samples are in the 30,000 Ph/MeV range, from radioluminescence measured with a silicon photodetector, their pulse heights with bialkali PMT readout are slightly less than that of the EJ208 sample. As in the beta light yield measurements, sample 2a is brighter than 2c in the gamma pulse height spectra (Compton edge shifted to higher channel number). It may be that, as mentioned earlier, BiPh$_3$ increases the proportion of triplet excitons in the system, which are longer lived and more likely to reach a fluor molecule before relaxing. FIG. 10 and FIG. 13 shows that the blue spectra from the EJ208 and the DPA-activated samples provide a higher effective light yield with PMT readout, compared to the green emission from the Ir-complex. Finally, the gamma spectra of the PVK/FIrpic/BiPh$_3$ and the PVK/FIrpic samples, 2a and 2c, were measured with an Am-241 source, with gamma energy of 59.5 keV. The intensity of the photopeak is about 25× stronger for the BiPh$_3$-containing sample, and the resolution is slightly better at 26%.

Figure 14:
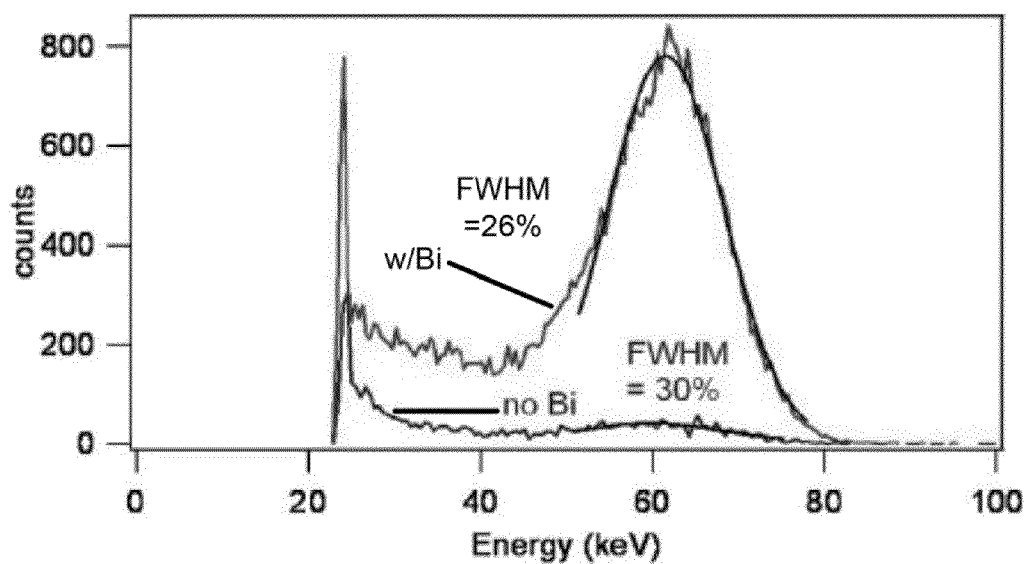
FIG. 14 is a graph showing the pulse height spectra acquired for an embodiment.

FIG. 14 shows the pulse height spectra acquired with an Am-241 source of sample 2a, of composition PVK/FIrpic/BiPh$_3$ and of sample 2c, of composition PVK/FIrpic reveal resolution at 59.5 keV of 26% and 30%, respectively. The higher effective Z of sample 2a produces a ~25× stronger photopeak at this energy.

Surprising Results

As noted above, and contrary to conventional wisdom and what one skilled in the art would have expected, the inventors have surprisingly found that it is possible to incorporate high-Z components into a polymer-based scintillator material and obtain resolutions that enable gamma ray spectroscopy. Moreover, the inventors have even more surprisingly found that performance of the scintillator may actually increase upon addition of the high-Z material.

Referring to FIG. 15, there are shown experimental results which support the foregoing statement. In this experiment, the polymer matrix was PVK, and the amount of fluor (iridium dye in this experiment) and high-Z component (BiPh$_3$ in this experiment) were varied. As shown in the first three rows, when no fluor was present, an increase in the amount of high-Z component diminished the light yield, as one would predict. Here, as the amount of high Z BiPh$_3$ is increased from 0% by weight to 25% and furthermore 40% by weight to the PVT sample, the light yield is quenched entirely.

Referring next to the middle three rows of FIG. 15, three samples were prepared, each having 1% by weight of fluor (again iridium dye in these samples) in a polymer (here PVK) matrix. In each sample, the amount of high-Z component (again BiPh$_3$ in these samples) was increased incrementally by weight. Surprisingly, and contrary to what would be expected by one skilled in the art, as the amount of high-Z component was increased, so did the light yield.

Referring next to the last three rows of FIG. 15, three samples were prepared, each having 3% by weight of fluor (again iridium dye in these samples) in a polymer (here PVK) matrix. In each sample, the amount of high-Z component (again BiPh$_3$ in these samples) was increased incrementally by weight. Surprisingly, and contrary to what would be expected by one skilled in the art, as the amount of high-Z component was increased, so did the light yield.

In view of this surprising discovery, this study has shown that, one embodiment of polyvinylcarbazole-based plastic scintillators loaded with up to 40% triphenyl bismuth and activated with standard singlet fluors as well as spin-orbit coupling fluors may be formed with excellent mechanical integrity and high transparency. The light yields obtained in this embodiment with the Iridium complex spin-orbit coupling fluor (FIrpic) is about 3× that of the standard fluor, and the energy resolution with this sample is superior, as well. Energy resolution measured for the FIrpic-activated sample at 59.5 and 662 keV are 26% and 6.8%, respectively. Without wishing to be bound to any theory, it is believed that although these results were acquired with small samples, larger volumes will offer equivalent performance to those reported here which would enable a wide range of uses for these embodiments of plastic scintillators, potentially replacing single crystals for some applications, and expanding the capabilities of plastic scintillators in applications where they are currently employed.

The description herein is presented to enable any person skilled in the art to make and use the invention and is provided in the context of particular applications of the invention and their requirements. Various modifications to the disclosed embodiments will be readily apparent to those skilled in the art and the general principles defined herein may be applied to other embodiments and applications without departing from the spirit and scope of the present invention. Thus, the present invention is not intended to be limited to the embodiments shown, but is to be accorded the widest scope consistent with the principles and features disclosed herein.

The program environment in which one embodiment of the invention may be executed illustratively incorporates one or more general-purpose computers or special-purpose devices such hand-held computers. Details of such devices (e.g., processor, memory, data storage, input and output devices) are well known and are omitted for the sake of clarity.

It should also be understood that the techniques of the present invention might be implemented using a variety of technologies. For example, the methods described herein may be implemented in software running on a computer system, or implemented in hardware utilizing one or more processors and logic (hardware and/or software) for performing operations of the method, application specific integrated circuits, programmable logic devices such as Field Programmable Gate Arrays (FPGAs), and/or various combinations thereof. In particular, methods described herein may be implemented by a series of computer-executable instructions residing on a storage medium such as a physical (e.g., non-transitory) computer-readable medium. In addition, although specific embodiments of the invention may employ object-oriented software programming concepts, the invention is not so limited and is easily adapted to employ other forms of directing the operation of a computer.

The invention can also be provided in the form of a computer program product comprising a physical computer readable medium having computer code thereon. A computer readable medium can include any physical medium capable of storing computer code thereon for use by a computer, including optical media such as read only and writeable CD and DVD, magnetic memory or medium (e.g., hard disk drive), semiconductor memory (e.g., FLASH memory and other portable memory cards, etc.), etc.

In Use

Embodiments of the present invention may be used in a wide variety of applications, and potentially any application in which high light yield and/or high resolution is useful.

Illustrative uses of various embodiments of the present invention include, but are not limited to, applications requiring radiation detection. Search, surveillance and monitoring of radioactive materials are a few such examples. Various embodiments can also be used in the nuclear fuel cycle, homeland security applications, nuclear non-proliferation, medical imaging, high energy physics facilities, etc.

Yet other uses include detectors for use in treaty inspections that can monitor the location of nuclear missile warheads in a nonintrusive manner. Further uses include implementation in detectors on buoys for customs agents at U.S. maritime ports, cargo interrogation systems, and instruments that emergency response personnel can use to detect or search for a clandestine nuclear device. Assessment of radiological dispersal devices is another application.

Further embodiments may include medical radiation detectors, e.g., to identify radioactive isotopes in patients (e.g. PET scanners) and for x-ray radiography.

While various embodiments have been described above, it should be understood that they have been presented by way of example only, and not limitation. Thus, the breadth and scope of a preferred embodiment should not be limited by any of the above-described exemplary embodiments, but should be defined only in accordance with the following claims and their equivalents.

What is claimed is:

1. A scintillator material, comprising:
   a polymer; and
   a bismuth component present in an amount greater than or equal to 18 wt %.

2. The scintillator material of claim 1, wherein the bismuth component is present in an amount from about 20 wt % to about 45 wt %.

3. The scintillator material of claim 1, wherein the polymer includes at least one of poly-vinyltoluene, polyvinyltriphenylamine, polyvinyltriphenylamine and polyvinylcarbazole.

4. The scintillator material of claim 1, wherein the polymer includes polyvinylcarbazole, wherein the bismuth component is comprises a compound selected from a group consisting of: a tritolyl bismuth compound, a tristyryl bismuth compound, a tri-aryl bismuth compound, a bismuth alkoxide compound, a bismuth di-aryl chloride compound and a mixed-ligand bismuth.

5. The scintillator material of claim 2, wherein the compound is-triphenyl bismuth.

6. The scintillator material of claim 1, wherein the bismuth component is structurally characterized as being copolymerized with the polymer.

7. The scintillator material of claim 1, wherein the bismuth component is not chemically coupled to any other component of the polymer.

8. The scintillator material of claim 1, further comprising an effective amount of a fluor.

9. The scintillator material of claim 8, wherein the fluor is an organic fluor.

10. The scintillator material of claim 8, wherein the fluor is present in an amount from about 0.1 wt % to about 3 wt %.

11. The scintillator material of claim 8, wherein the fluor is an organometallic fluor.

12. The scintillator material of claim 1, further comprising:
    a fluor having a decay time of less than about 10 microseconds and greater than about 100 picoseconds,
    wherein the fluor is present in an amount from about 0.1 wt % to about 3 wt %,
    wherein the bismuth component comprises triphenyl bismuth,
    wherein the triphenyl bismuth is present in an amount from about 20 wt % to about 45 wt %,
    wherein the scintillator material is formed into a three dimensional structure, and
    wherein the three dimensional structure is characterized by at least two perpendicularly oriented dimensions, each of the perpendicularly oriented dimensions being about at least one centimeter in length.

13. The scintillator material of claim 11, wherein the organometallic fluor is an iridium complex fluor.

14. The scintillator material of claim 1, further comprising an effective amount of at least two different fluors.

15. The scintillator material of claim 14, wherein one of the fluors is an organometallic fluor.

16. The scintillator material of claim 1, wherein the bismuth component comprises triphenyl bismuth.

17. A scintillator radiation detector system, comprising:
    a scintillator material as recited in claim 1; and
    a processing device for processing pulse traces corresponding to light pulses from the scintillator material.

18. A scintillator radiation detector system, comprising:
    a scintillator material as recited in claim 1; and
    a processing device for generating radiological image data based on pulse traces corresponding to light pulses from the scintillator material.

19. A scintillator material, comprising:
    a polymer having a fluor incorporating therewith; and
    a bismuth component present in an amount greater than or equal to 18 wt %,
    wherein the scintillator material is formed into a three dimensional structure, and
    wherein the three dimensional structure is characterized by at least two perpendicularly-oriented dimensions, each of the perpendicularly-oriented dimensions being at least about one centimeter in length.

20. The scintillator material of claim 19, wherein the polymer includes at least one of poly-styrene, poly-vinyltoluene, polyvinyltriphenylamine, polyvinyltriphenylamine and polyvinylcarbazole.

21. The scintillator material of claim 19, wherein the bismuth component is selected from a group consisting of: a triphenyl bismuth compound, a tritolyl bismuth compound, a tristyryl bismuth compound, a tri-aryl bismuth compound, a bismuth alkoxide compound, a bismuth di-aryl chloride compound and a mixed-ligand bismuth compound, and
    wherein the bismuth component is present in an organometallic complex that is incorporated into the polymer.

22. The scintillator material of claim 19, wherein the bismuth component comprises triphenyl bismuth.

23. The scintillator material of claim 19, wherein the fluor is an organic fluor.

24. The scintillator material of claim 19, wherein the fluor is an organometallic fluor.

25. The scintillator material of claim 19, wherein the bismuth component is a triphenyl bismuth compound, wherein the triphenyl bismuth compound is present in an amount of between about 25 wt % and about 45 wt %.

26. The scintillator material of claim 24, wherein the organometallic fluor is an iridium complex fluor.

27. The scintillator material of claim 19, further comprising an effective amount of at least two different fluors.

28. The scintillator material of claim 19, wherein the polymer includes a polymeric component having a bandgap of less than that of poly-vinyltoluene.

29. A scintillator radiation detector system, comprising:
a scintillator material as recited in claim 19; and
a processing device for processing pulse traces corresponding to light pulses from the scintillator material.

30. A method, comprising:
processing pulse traces corresponding to light pulses from a scintillator material,
the scintillator material comprising:
a polymer; and
a bismuth component present in an amount greater than or equal to 18 wt %, outputting a result of the processing.

31. A method, comprising:
mixing a bismuth organometallic complex with monomer or polymer and at least one fluor; and
processing the mixture for creating a scintillator material comprising:
a polymer; and
a bismuth component present in an amount greater than or equal to 18 wt %.

32. The method of claim 31, wherein the bismuth organometallic complex is copolymerized with the monomer to form the scintillator material, and
wherein the bismuth component comprises a triphenyl bismuth compound.

33. The method of claim 31, wherein the processing includes causing the monomer or polymer to crosslink,
wherein the bismuth organometallic complex is not chemically coupled to any other component of the scintillator material, and
wherein the bismuth component comprises a compound selected from a group consisting of: the triphenyl bismuth compound, a tritolyl bismuth compound, a tristyryl bismuth compound, a tri-aryl bismuth compound, a bismuth alkoxide compound, a bismuth di-aryl chloride compound and a mixed-ligand bismuth compound.

* * * * *